(12) United States Patent
Yamashita

(10) Patent No.: US 6,777,214 B1
(45) Date of Patent: Aug. 17, 2004

(54) METHOD FOR CONTROLLING ORGANISMS AND MATERIAL THEREFOR, METHOD FOR SELECTIVE ADSORPTION OF PROTEINS AND MATERIAL THEREFOR, CEMENT MATERIAL AND BIOMATERIAL

(75) Inventor: Kimihiro Yamashita, Tokyo-to (JP)

(73) Assignee: Yuugen Gaisha Neichamateriaru, Ehime-Ken (JP)

( * ) Notice: Subject to any disclaimer, the term of this patent is extended or adjusted under 35 U.S.C. 154(b) by 0 days.

(21) Appl. No.: 09/533,150

(22) Filed: Mar. 23, 2000

(30) Foreign Application Priority Data

Mar. 23, 1999 (JP) .......................................... 11-077089
Jan. 12, 2000 (JP) ...................................... 2000-003545

(51) Int. Cl.[7] ............................................ C12N 13/00
(52) U.S. Cl. ............................... 435/173.1; 435/173.7; 435/173.9; 501/1; 423/299; 423/308
(58) Field of Search .......................... 435/173.1, 173.7, 435/173.9; 501/1; 423/299, 308

(56) References Cited

U.S. PATENT DOCUMENTS 2,976,246 A    3/1961  Egerton et al.

FOREIGN PATENT DOCUMENTS

| JP | 62-72373   | 4/1987  |
| JP | 7-284527   | 10/1995 |
| JP | 9-329602   | 12/1997 |
| JP | 10-324584  | 12/1998 |

OTHER PUBLICATIONS

File Medline On Stn. Abstract No. (AN NO.)92212356. Moriya et al. 'Experimental Study on the Application of Direct Current to the Intra–Osseous Implant', Nippon Hotetsu Shika Gakkai Zasshi vol. 34, No. 2, (Apr. 1990), pp. 309–317. Abstract Only.*

Kobayashi et al. 'Vectorial Effects on Tissue Reaction of Electrically Poled Hydroxyapatite Ceramic', Bioceramics, Proceedings of the 12th International Symposium on Ceramics in Medicine, vol. 12, pp. 291–294. Oct. 1999.*

Jianqing, F. et al., "Promotion Of Osteogenesis By A Piezoelectric Biological Ceramic," *Biomaterials*, Elsevier Science Publishers B.V., Barking, GB, vol. 18, No. 23, Dec. 1, 1997, pp. 1531–1534.

Park, J.B. et al., "Piezoelectric Ceramic Implants: In Vivo Results", *J. Biomed. Mater. Res.*, vol. 15, No. 1, Jan. 1981, pp. 103–110.

Feng, J. et al., "An Investigation On The Ceramic Composite Of Th e Biological Piezoelectric Implants", Feng; H., *Polymers and Biomaterials*, Elsevier Science Publishers, B.V., Amsterdam, 1991, pp. 367–371.

Kimihiro Yamashita et al., "Acceleration and Deceleration of Bone–Like Crystal Growth on Ceramic Hydroxyapatite by Electric Poling," *Chem. Mater.*, vol. 8, No. 12, pp. 2697–2700, 1996.

* cited by examiner

Primary Examiner—Brenda Brumback
Assistant Examiner—Anish Gupta
(74) Attorney, Agent, or Firm—Price, Heneveld, Cooper, DeWitt & Litton, LLP

(57) ABSTRACT

A method for controlling organisms which comprises growing, decreasing, activating or inactivating cells, bacteria, viruses or fungi at an N-surface or a P-surface of a ceramic which is formed by treating the ceramic by polarization; and a material for controlling organisms, a method for selective adsorption of proteins, a material for selective adsorption of proteins, a cement material for filling bones and dental applications and a biomaterial, in which the ceramic treated by polarization is utilized.

By utilizing difference in properties among surfaces of the ceramic treated by polarization, growth, decrease, activation or inactivation of organisms such as cells, bacteria, viruses or fungi can be controlled. Therefore, the above methods and materials are useful in the medical, dental and biochemical areas.

3 Claims, 16 Drawing Sheets

Control (Cell culture dish)

Negatively charged surface

Positively charged surface

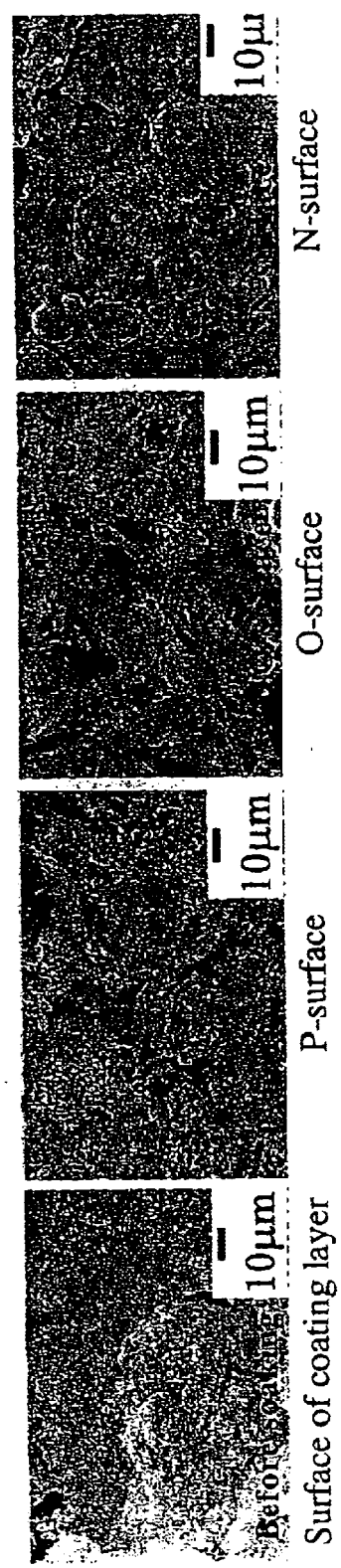
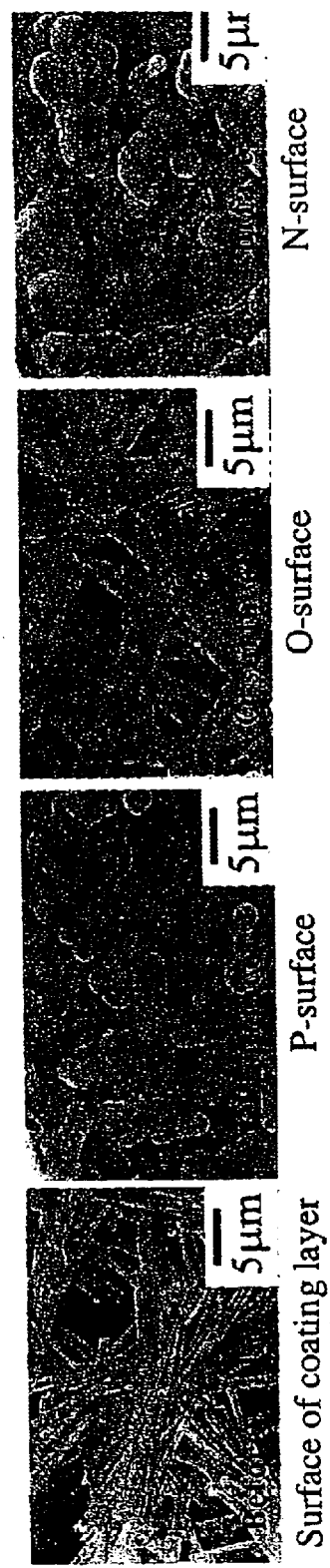
FIG. 14
FIG. 15

METHOD FOR CONTROLLING ORGANISMS AND MATERIAL THEREFOR, METHOD FOR SELECTIVE ADSORPTION OF PROTEINS AND MATERIAL THEREFOR, CEMENT MATERIAL AND BIOMATERIAL

BACKGROUND OF THE INVENTION

1. Field of the Invention

The present invention relates to a ceramic (including powder and fiber) treated by polarization and, more particularly, to a method for growing, decreasing, activating or inactivating cells, bacteria or the like and a material therefor, in which a ceramic treated by polarization is utilized.

The present invention also relates to a method for selective adsorption of proteins by utilizing difference in the absorption properties among surfaces of a ceramic which are formed by treating the ceramic by polarization and a material therefor.

The present invention further relates to a cement material for filling bones and dental applications which comprises powder of a ceramic treated by polarization.

2. Description of Related Art

It has been proposed by the present inventors in Japanese Patent Application Laid-Open No. Heisei 10(1998)-324584 that a ceramic, an inorganic material, having affinity to biomaterials which is obtained by treating a ceramic by polarization can be used as a tooth material to reinforce or replace a tooth bone and increases the growth rate of crystals similar to bone materials.

SUMMARY OF THE INVENTION

An object of the present invention is to provide a method for controlling organisms, i.e., growing, decreasing, activating and inactivating cells and tissues of organisms, which can be applied to a wide range of areas such as the medical, dental and biochemical areas and to antibiotic applications and a material therefor, a method for selective adsorption of proteins and a material therefor and a cement material for filling bones and dental applications.

The present invention provides:

(1) A method for controlling organisms which comprises growing, decreasing, activating or inactivating cells, bacteria, viruses or fungi at an N-surface or a P-surface of a ceramic which is formed by treating the ceramic by polarization;

(2) A material for controlling organisms which is a ceramic treated by polarization so that cells, bacteria, viruses or fungi are grown, decreased, activated or inactivated at an N-surface or a P-surfaces of the ceramic which is formed by the treatment;

(3) A method for selective adsorption of proteins which comprises selectively adsorbing drugs, nutrients and proteins by utilizing difference in adsorption properties among an N-surface, an O-surface and a P-surface of a ceramic which are formed by treating the ceramic by polarization;

(4) A material for selective adsorption of proteins which is a ceramic treated by polarization so that drugs, nutrients and proteins are selectively adsorbed due to difference in adsorption properties among an N-surface, an O-surface and a P-surface of a ceramic which are formed by treating the ceramic;

(5) A cement material for filling bones and dental applications which comprises powder or fiber of a ceramic treated by polarization;

(6) A biomaterial which is obtained by treating a ceramic having affinity to biomaterials by polarization in an atmosphere of steam at a temperature from a room temperature to 1,000° C.; and (7) A biomaterial which is obtained by treating a ceramic having affinity to biomaterials by polarization at a voltage from 10 to 100,000 V/cm.

BRIEF DESCRIPTION OF THE DRAWINGS

FIG. 14 is a microscopic photograph exhibiting an embodiment of another example of the present invention.

FIG. 15 is a microscopic photograph exhibiting another embodiment of another example of the present invention.

Figure 1:
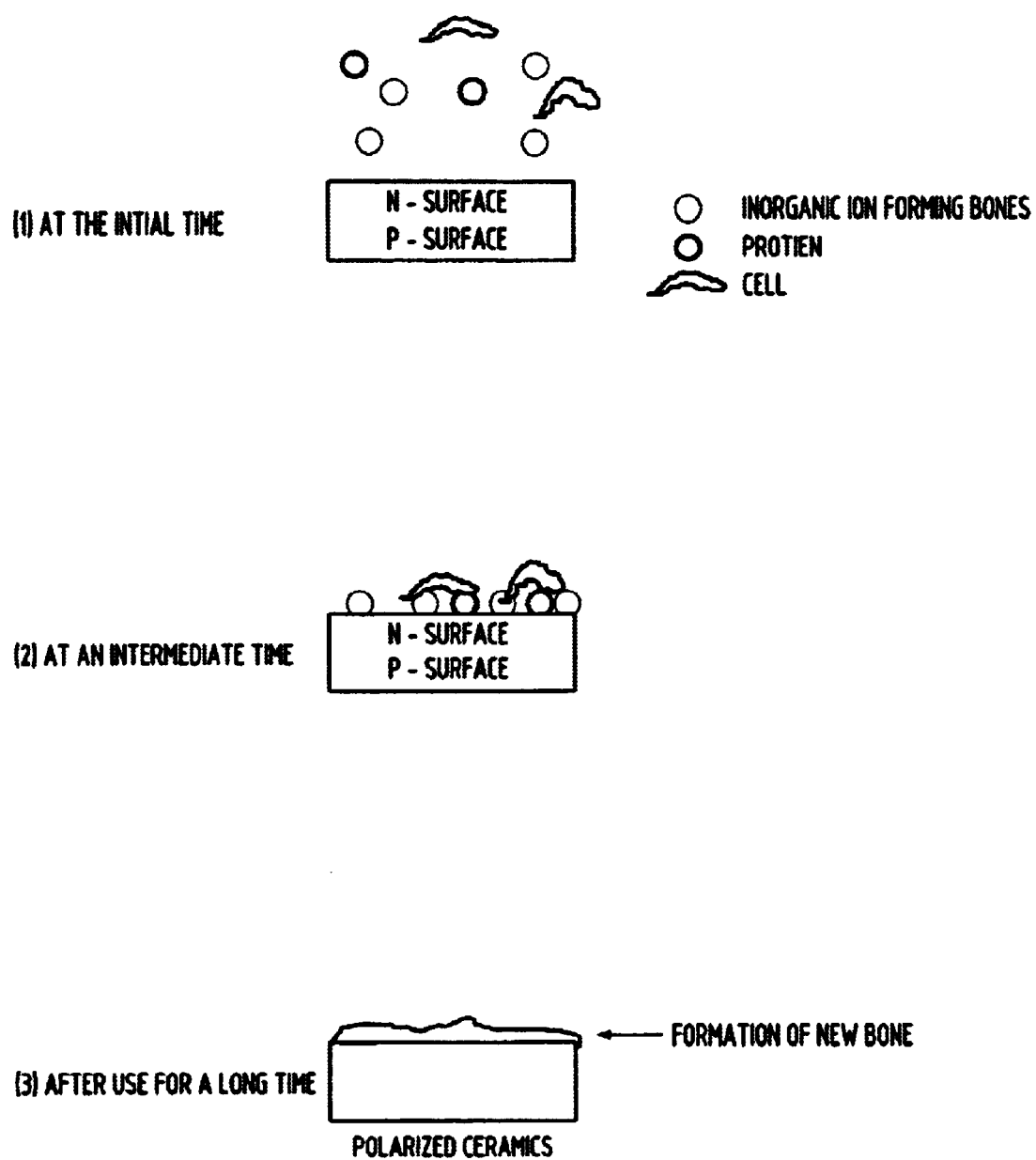
FIG. 1 is a diagram exhibiting the principle of the present invention.

The numbers in the above figures have the following meanings:

1: A ceramic treated by polarization (a space formed by removing the ceramic)
2: An N-surface
3: A newly formed bone
4: A P-surface
5: A cell similar to a connective tissue
6: An osteoblast
7: Medulla ossium
8: A barium titanate ceramic (a space formed by removing the ceramic)

9: A cortical bone
10: A productive cell
11: A liver cell
12: Cells arranged in order
13: Cells arranged in disorder
14: An O-surface

DESCRIPTION OF THE PREFERRED EMBODIMENTS

The present invention provides a method for controlling organisms which comprises growing, decreasing, activating or inactivating cells, bacteria, viruses or fungi at the N-surface or the P-surface of a ceramic which is formed by treating the ceramic by polarization.

The present invention also provides the method for controlling organisms, wherein the ceramic is a material or a combination of materials selected from hydroxyappatite ceramics, barium titanate ceramics, strontium hydroxyappatite ceramics, hydroxyappatite ceramics containing calcium or strontium as solid solutions lithium niobate ceramics, sodium niobate ceramics, potassium niobate ceramics, glasses and crystallized glasses which contain calcium phosphate, stabilized and partially stabilized zirconia ceramics, ion conductive alumina (so-called β-alumina) ceramics, and piezoelectric ceramics containing lead.

The present invention also provides the method for controlling organisms wherein the ceramic is powder, fiber or a coating film.

The present invention provides a material for controlling organisms which is a ceramic treated by polarization so that cells, bacteria, viruses or fungi are grown, decreased, activated or inactivated at the N-surface or the P-surfaces of the ceramic which is formed by the treatment.

The present invention also provides the material for controlling organisms wherein the ceramic is a material or a combination of materials selected from hydroxyappatite ceramics, barium titanate ceramics, strontium hydroxyappatite ceramics, hydroxyappatite ceramics containing calcium or strontium as solid solutions, lithium niobate ceramics, sodium niobate ceramics, potassium niobate ceramics, glasses and crystallized glasses which contain calcium phosphate, stabilized and partially stabilized zirconia ceramics, ion conductive alumina (so-called β-alumina) ceramics, and piezoelectric ceramics containing lead.

The present invention also provides the material for controlling organisms wherein the ceramic is powder, fiber or a coating film.

At the N-surface of a ceramic treated by polarization, osteoblasts grow and ossification proceeds rapidly. Therefore, damages on a bone can be recovered rapidly when a material for filling bones or an artificial bone is covered with powder of a ceramic treated by polarization or is coated with a film of a ceramic treated by polarization. When an implant material for orthopaedic surgery and dental treatments which is made of a metal such as titanium or a polymer and coated with a ceramic having affinity to biomaterials on the surface is used after the treatment by polarization, osteoblasts grow at the N-surface of the ceramic treated by polarization and ossification proceeds rapidly. Thus, the ability to recover is enhanced.

As described above, in the clinical application of the ceramic treated by polarization in accordance with the present invention, ossification proceeds at the N-surface in the early stage of about one week when the ceramic is used as an implant material of articulatio coxa or an artificial radix dentis. This surgically very important property, which is called early fixing, is not found in conventional materials and has attracted attention. Moreover, the advantage of the material in accordance with the present invention is not limited to the above. In clinical applications for longer periods of several weeks to several months, or still longer, it is confirmed that ossification proceeds at the P-surface to about the same extent with that at the N-surface. Based on this knowledge, it is confirmed in the clinical application of the ceramic treated by polarization in accordance with the present invention that the ceramic can be used not only as the implant material but also in other applications such as retaining bones in osteoporosis.

FIG. 1 is a diagram exhibiting the principle of the present invention. At the N-surface or the P-surface of the ceramic treated by polarization, cells of an organism are adsorbed together with inorganic ions and proteins for ossification. These substances are embedded and stay there for a long time and form a new bone. The mechanism for the ossification has not been elucidated. The ossification may arise based on the property of genes, the properties of proteins at the surface of the cells or the properties of the inside of the cells or from other causes. The mechanism is under an intensive study.

In the inside of an organism, the N-surface or the P-surface of the ceramic treated by polarization can affect cells and tissues of organisms so that cells of the organisms, immunization cells and lymph corpuscles are grown, cell tissues and nerve cells are activated and various tissues and cells are regenerate and grown. Conventional cell incubators made of a polymer or glass have problems such as elution of the material of the incubators. When a material coated with the ceramic which has affinity to biomaterials and is treated by polarization is used as the material for an incubator, the obtained incubator exhibits a great effect of promoting growth of cells and tissues.

The N-surface or the P-surface of the ceramic treated by polarization affects bacteria or viruses so that bacteria or viruses are grown and activated. Therefore, a material for an incubator exhibiting a great effect of promoting growth of bacteria or viruses can be obtained.

On the other hand, bacteria, viruses or fungi may be decreased or inactivated on both or either one of the N-Surface and the P-surface of the ceramic treated by polarization. This behavior may be different depending on the type of microorganisms. Therefore, antimicrobial food wares and various types of antimicrobial instruments can be prepared by using the N-surface and the P-surface of the ceramic formed by the treatment by polarization separately in various ways.

Figure 2:
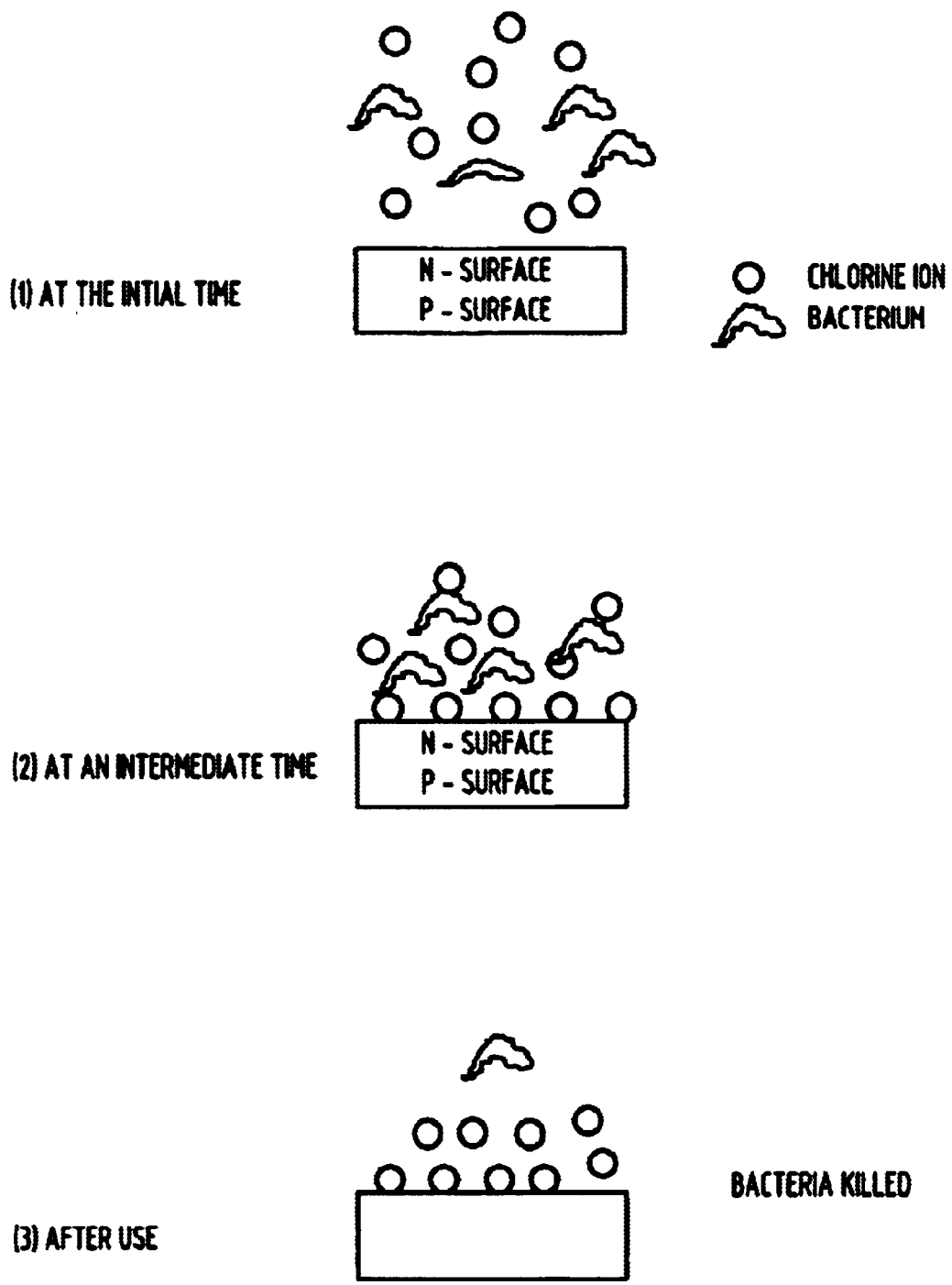
FIG. 2 is a diagram exhibiting the principle of the present invention.

FIG. 2 is a diagram exhibiting a model showing the antimicrobial effect. To the P-surface of the ceramic treated by polarization, bacteria are adsorbed together with chlorine ion and the bacteria are killed by the chlorine ion. Thus, the antimicrobial effect is exhibited.

The present invention provides the method for selective adsorption of proteins which comprises selectively adsorbing drugs, nutrients and proteins by utilizing difference in adsorption properties among the N-surface, the O-surface (a neutral surface placed between the N-surface and the P-surface) and the P-surface of a ceramic which are formed by treating the ceramic by polarization.

The present invention also provides the material for selective adsorption of proteins which is a ceramic treated by polarization so that drugs, nutrients and proteins are selectively adsorbed due to difference in adsorption properties among the N-surface, the O-surface and the P-surface of the ceramic which are formed by treating the ceramic.

The present invention also provides the material for selective adsorption for proteins wherein the ceramic is a material or a combination of materials selected from hydroxyappatite ceramics, barium titanate ceramics, strontium hydroxyappatite ceramics, hydroxyappatite ceramics containing calcium or strontium as solid solutions, lithium niobate ceramics, sodium niobate ceramics, potassium niobate ceramics, glasses and crystallized glasses which contain calcium phosphate, stabilized and partially stabilized zirconia ceramics, ion conductive alumina (so-called β-alumina) ceramics, and piezoelectric ceramics containing lead.

As the surfaces of the ceramic treated by polarization, the N-surface, the P-surface and the O-surface having no polarity as the boundary between the N-surface and the P-surface are present. The selective adsorption of drugs, nutrients and proteins can be achieved by taking advantage of the difference in the adsorption properties among the N-surface, the O-surface and the P-surface. By soaking the ceramic into a solution or by placing the ceramic inside a tissue, various types of drugs, nutrients and proteins can be selectively adsorbed to the different surfaces in accordance with the types and are separated with respect to the types. The ceramic can also be used as a sensor which detects the presence of a specific drug or the like.

As described above, in accordance with the present invention, organisms such as cells, bacteria, viruses or fungi can be grown, decreased, activated or inactivated at the N-surface or the P-surface of the ceramic which is formed by the treatment by polarization. Moreover, the control of organisms can be conducted in a desired manner by suitably selecting the ceramic treated by polarization with respect to the amount of the stored polarization energy and the type of the ceramic.

In the present invention, controlling organisms means controlling, i.e., growing, decreasing, activating, inactivating or the like, organisms such as cells, bacteria, viruses, fungi and the like.

The present invention also provides a cement material for filling bones and dental applications which comprises powder or fiber of a ceramic treated by polarization.

The powder of the ceramic treated by polarization exhibits great chemical reactivity. Therefore, the above cement can be hardened more rapidly than conventional dental cements or orthopedic cements and exhibits a greater strength. By using the powder of the ceramic treated by polarization singly or as a mixture with conventional cement materials, an excellent cement material which is rapidly hardened and exhibits a great strength can be provided.

The present invention also provides the cement material which comprises needle-shaped powder or fiber of a ceramic treated by polarization.

The needle-shaped powder or fiber of the ceramic shows a greater degree of entanglement due to the elongated shape and provides a dental cement or an orthopedic cement exhibiting a greater reinforcing effect.

The needle-shaped powder and the fiber are formed on the surface of a metal such as titanium and aluminum on which scratches are formed in accordance with the biomimetic coating method. The mechanism of the formation of the needle-shaped powder or the fiber has not been elucidated. The unstable condition of the surface having scratches may lead to the formation of the needle-shaped materials rather than an appatite layer.

Examples of the method for coating a substrate with the ceramic include the biomimetic method, the plasma spray method, the sputtering method, the electrophoretic deposition followed by sintering, the dip-coating method and the functionally gradient composite coating method. In accordance with the biomimetic method, various substrates are coated with appatite coatings by utilizing the principle of formation of bones in organisms. Into a solution (a simulated body fluid) having pH of 7.25 and concentrations of ions adjusted to about the same values as those in the human body fluid, a substrate and a glass containing calcium and silica as the main components are soaked for 1 to 4 days at 36.5° C. Silicate ion eluted from the glass is attached to the surface of the substrate and absorbs calcium ion and phosphate ion in the solution to form an appatite layer. The surfaces of metals, ceramics and macromolecular synthetic resins can be coated with appatite in accordance with this method.

The present invention also provides a cement material wherein the ceramic is a material or a combination of materials selected from hydroxyappatite ceramics, barium titanate ceramics, strontium hydroxyappatite ceramics, hydroxyappatite ceramics containing calcium or strontium as solid solutions, lithium niobate ceramics, sodium niobate ceramics, potassium niobate ceramics, glasses and crystallized glasses which contain calcium phosphate, stabilized and partially stabilized zirconia ceramics, ion conductive alumina (so-called β-alumina) ceramics, and piezoelectric ceramics containing lead.

The present invention also provides a biomaterial which is obtained by treating a ceramic having affinity to biomaterials by polarization in an atmosphere of steam at a temperature from a room temperature to 1,000° C. at a voltage of 10 to 100,000 V/cm.

The ceramic can be treated by polarization at a temperature lower than the room temperature or at a voltage lower than 10 V/cm. However, it takes a long time for the polarization and the amount of the energy stored in the ceramic is small. The ceramic can be treated by polarization at a temperature higher than 1,000° C. or a voltage higher than 100,000 V/cm. However, the energy is not stored in the ceramic but lost as the current which flows out and the amount of the energy stored in the ceramic is smaller than the expected amount. Therefore, from the standpoint of the time for the treatment by polarization and the amount of the stored energy, it is preferable that the biomaterial is obtained by treatment by polarization in the condition of a temperature from a room temperature to 1,000° C. and a voltage from 10 to 100,000 V/cm.

The optimum condition for the treatment by polarization is different depending on the type of the ceramic for the polarization and can be obtained by repeating ordinary experiments with respect to individual ceramics.

The present invention also provides the biomaterial wherein the ceramic is a material or a combination of materials selected from hydroxyappatite ceramics, barium titanate ceramics, strontium hydroxyappatite ceramics, hydroxyappatite ceramics containing calcium or strontium as solid solutions, lithium niobate ceramics, sodium niobate ceramics, potassium niobate ceramics, glasses and crystallized glasses which contain calcium phosphate, stabilized and partially stabilized zirconia ceramics, ion conductive alumina (so-alled β-alumina) ceramics, and piezoelectric ceramics containing lead.

Strontium hydroxyappatite and hydroxyappatite ceramics containing calcium or strontium as solid solutions are successfully synthesized by sintering powder prepared in accordance with a wet synthesis process by heating in steam in a condition such that the lattice OH⁻ is not vaporized, for example at 1200° C. for 1 to 5 hours.

The solid solution described above means a mixture obtained by mixing components without destroying the structure or a mixture in the condition obtained by such mixing.

The advantages of the present invention are summarized in the following.

As will be specifically shown with reference to examples, at the N-surface of the ceramic treated by polarization in accordance with the present invention, osteoblast grows in the early stage of about one week and ossification proceeds rapidly. At the P-surface of the ceramic, ossification proceeds in a manner similar to that at the N-surface over a longer period of several weeks to several months. Therefore, by applying powder or fiber of the ceramic treated by polarization or a film coated with the ceramic treated by polarization to fillers for bones or artificial bones, recovery of the bones can be achieved rapidly and surely. This method can be applied to retaining bones in osteoporosis. By using an implant material for orthopaedic surgery and dental treatments in which the surface of a metal such as titanium or a polymer is coated with the ceramic having affinity to biomaterials after the treatment by polarization, osteoblast grows in the early stage of about one week and ossification proceeds rapidly at the N-surface or the P-surface of the ceramic treated by polarization and the ability of recovery increases.

The N-surface or the P-surface of the ceramic treated by polarization can affect cells and tissues of organisms so that cells of the organisms, immunization cells and lymph corpuscles are grown, cell tissues and nerve cells are activated and various tissues and cells are regenerated and grown.

Conventional cell incubators made of a polymer or glass have problems such as elution of the material. When a material coated with the ceramic which has affinity to biomaterials and is treated by polarization is used as the material for an incubator, the obtained incubator exhibits a great effect of promoting growth of cells and tissues.

The N-surface or the P-surface of the ceramic treated by polarization affects bacteria or viruses so that bacteria or viruses are grown and activated. Therefore, a material for an incubator exhibiting a great effect of promoting growth of bacteria or viruses can be obtained.

On the other hand, bacteria, viruses or fungi may be decreased or inactivated on both or either one of the N-Surface and the P-surface of the ceramic treated by polarization. This behavior may be different depending on the type of microorganisms. Therefore, antimicrobial food wares and various types of antimicrobial instruments can be prepared by using the N-surface and the P-surface of the ceramic formed by the treatment by polarization separately in various ways.

As the surfaces of the ceramic treated by polarization, the N-surface, the P-surface and the O-surface having no polarity as the boundary between the N-surface and the P-surface are present. The selective adsorption of drugs, nutrients and proteins can be achieved by taking advantage of the difference in the adsorption properties among the N-surface, the O-surface and the P-surface. By soaking the ceramic into a solution or by placing the ceramic inside a tissue, various types of drugs, nutrients and proteins can be selectively adsorbed to the different surfaces in accordance with the types and are separated with respect to the types. The ceramic can also be used as a sensor which detects the presence of a specific drug or the like.

As described above, the method for controlling organisms which comprises growing, decreasing, activating or inactivating cells, bacteria, viruses or fungi at an N-surface or a P-surface of a ceramic which is formed by treating the ceramic by polarization and the material therefor are provided.

The powder of the ceramic treated by polarization exhibits great chemical reactivity. Therefore, the powder can be hardened more rapidly than conventional dental cements and orthopedic cements and exhibits a greater strength. By using the powder of the ceramic treated by polarization singly or as a mixture with conventional cement materials, an excellent cement material which is rapidly hardened and exhibits a great strength can be provided.

The needle-shaped powder or fiber of the ceramic shows a greater degree of entanglement due to the elongated shape and provides a dental cement or an orthopedic cement exhibiting a greater reinforcing effect.

The biomaterial advantageous from the standpoint of the time for the treatment by polarization and the amount of the stored energy can be obtained by treating a ceramic having affinity to biomaterials by polarization in an atmosphere of steam at a temperature from a room temperature to 1,000° C. at a voltage from 10 to 100,000 V/cm.

EXAMPLES

The present invention will be described more specifically with reference to examples exhibited by figures in the following.

Figure 3:
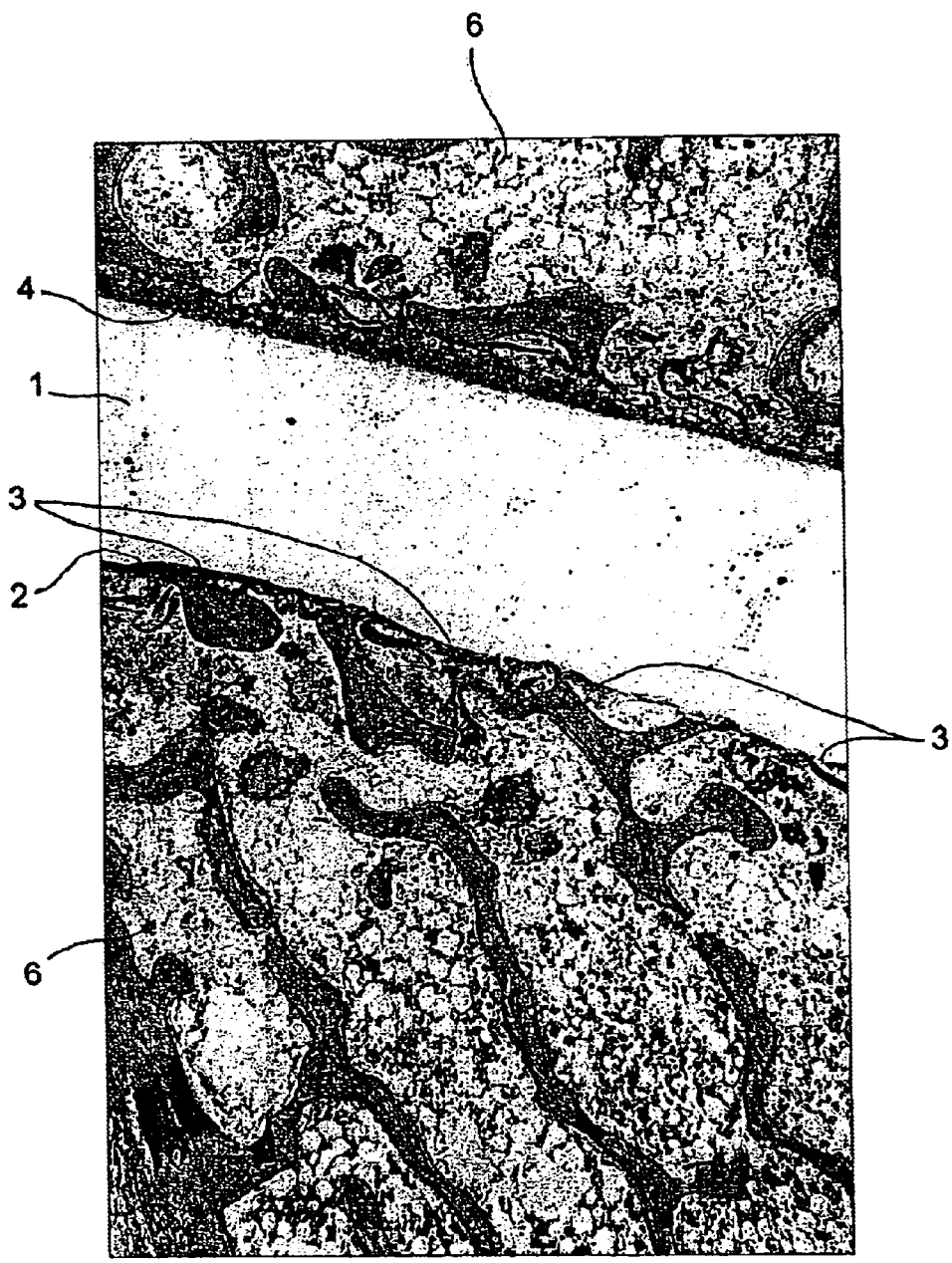
FIG. 3 is a microscopic photograph exhibiting an embodiment of an example of the present invention.
Figure 4:
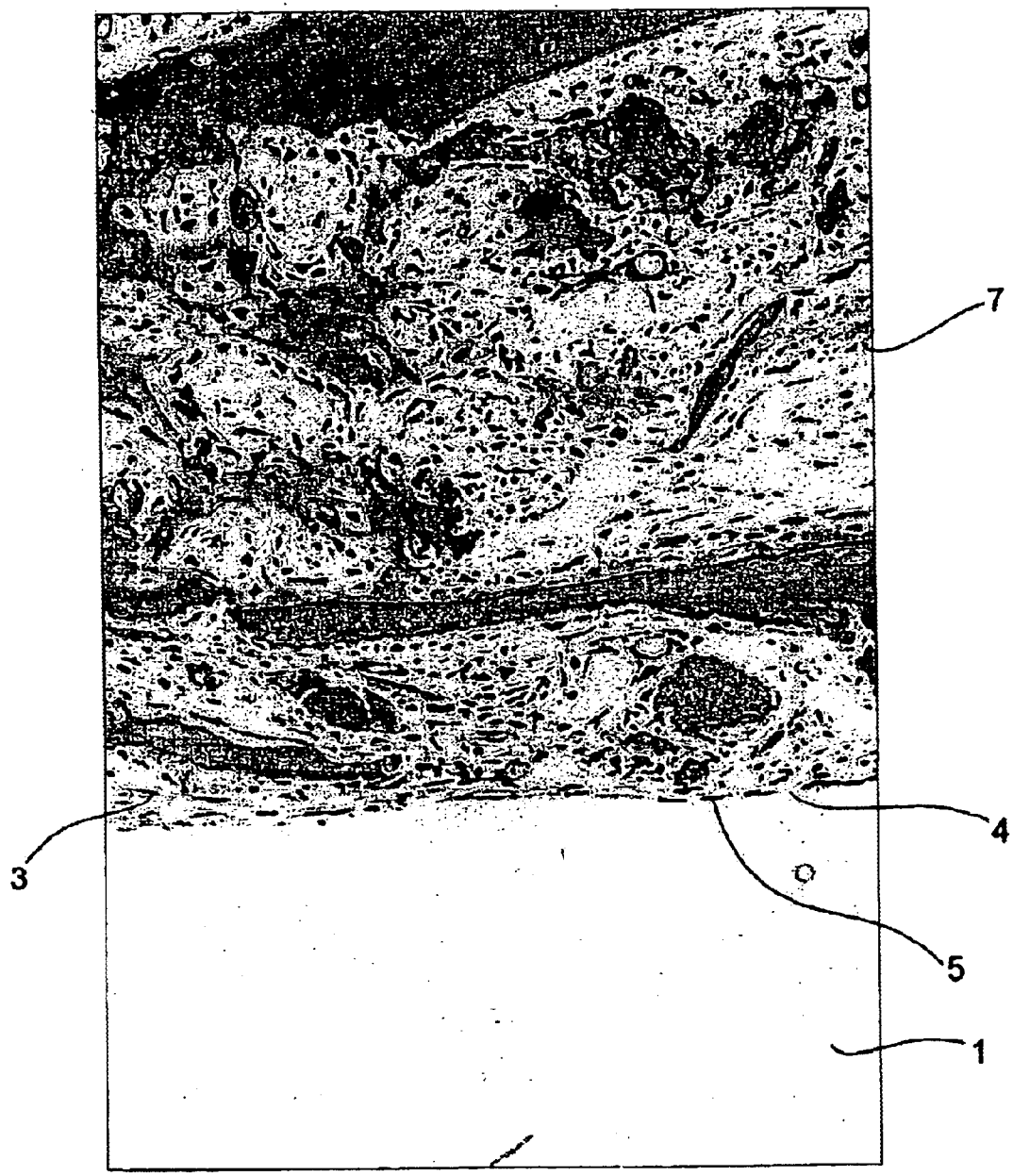
FIG. 4 is a microscopic photograph exhibiting another embodiment of an example of the present invention.
Figure 5:
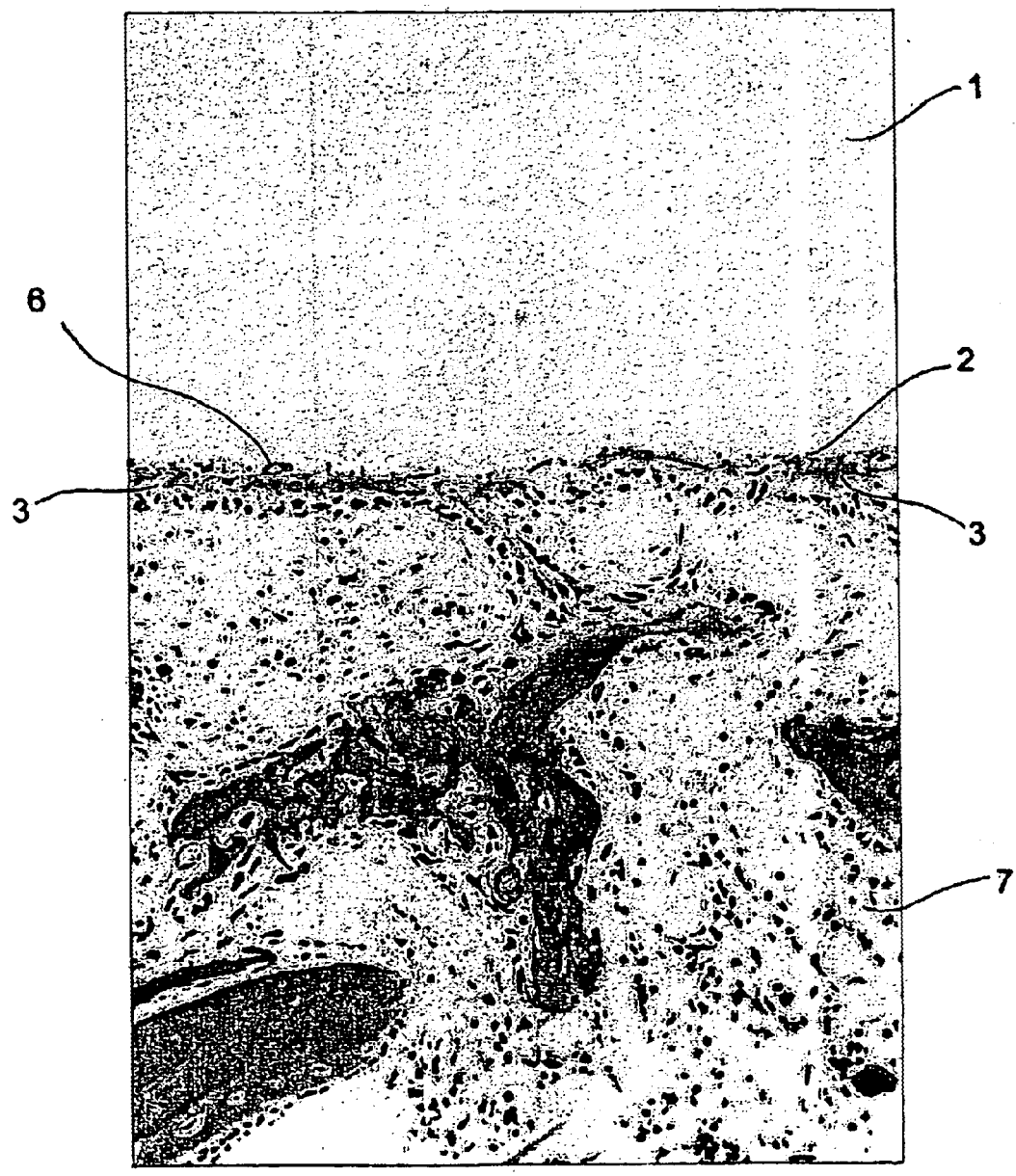
FIG. 5 is a microscopic photograph exhibiting another embodiment of an example of the present invention.

FIGS. 3 to 5 are photographs exhibiting the reaction of living tissues when a hydroxyappatite ($Ca_{10}(PO_4)_6(OH)_2$) ceramic treated by polarization is embedded inside medulla ossium of an adult beagle. FIG. 3 is a photograph magnified 200 times. Newly formed bones 3 are found at the N-surface 2 of the hydroxyappatite and bleeding is found at the P-surface 4.

FIG. 4 is a photograph exhibiting another P-surface 4 which is magnified 400 times. A newly formed bone 3 is found at a position separated from the P-surface. Cells 5 having a long cytoplasm which are similar to connective tissues are arranged in the vicinity of the P-surface.

FIG. 5 is a photograph exhibiting another N-surface 2 which is magnified 400 times. A newly formed bone 3 is found at a position adjacent to the N-surface 2. The cell of a single layer adjacent to the N-surface 2 is considered to be an osteoblast 6. 7 shows medulla ossium and shows the space formed by removing the ceramic.

Figure 6:
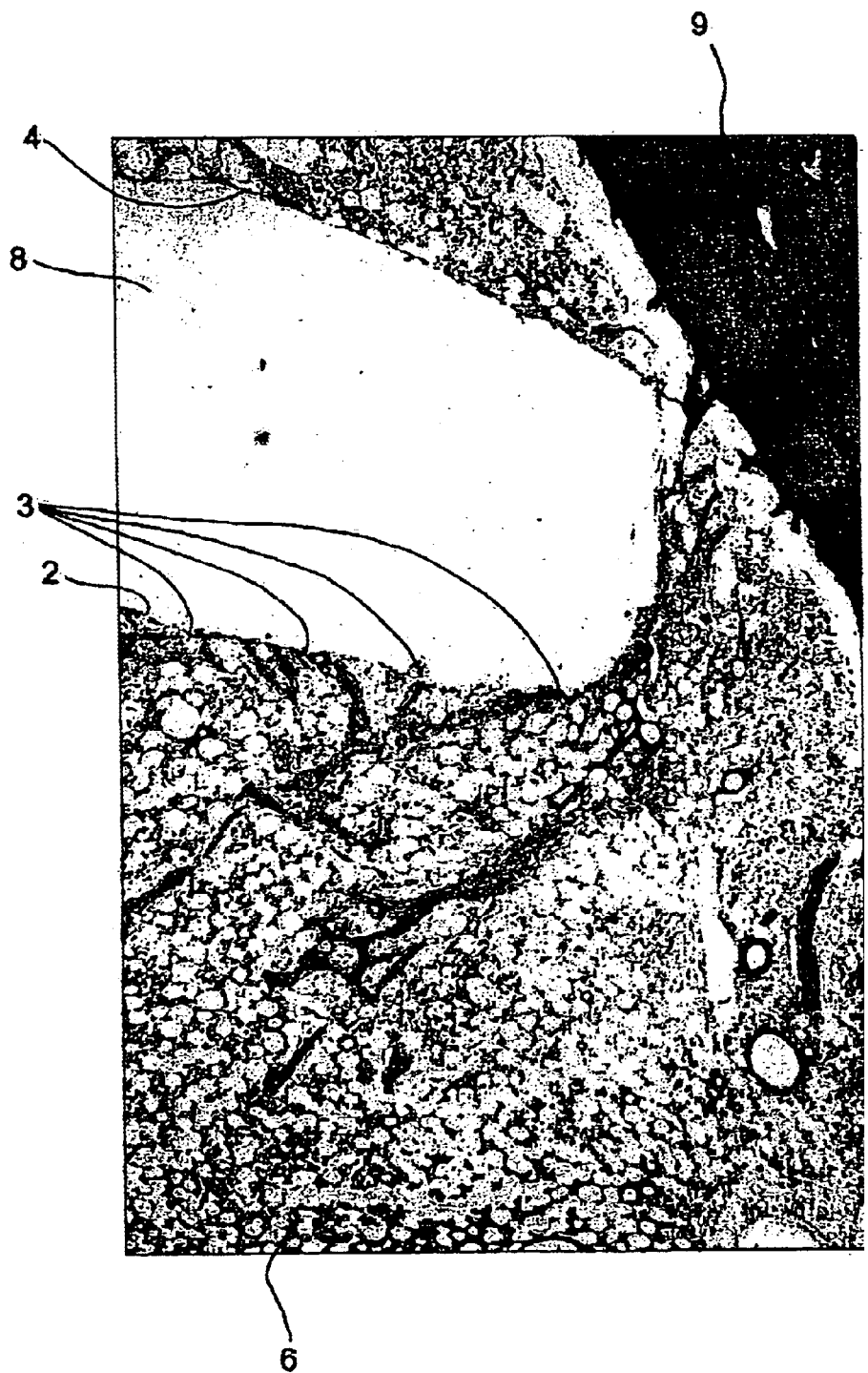
FIG. 6 is a microscopic photograph exhibiting another embodiment of an example of the present invention.

FIG. 6 is a photograph magnified 200 times which exhibits the reaction of living tissues when a barium titanate ceramic 8 is placed inside medulla ossium 6 of an adult beagle for 7 days. Newly formed bones 3 with protrusions are found along the N-surface 2. In contrast, almost no newly formed bones are found at the P-surface 4. 9 shows a cortical bone.

Figure 7:
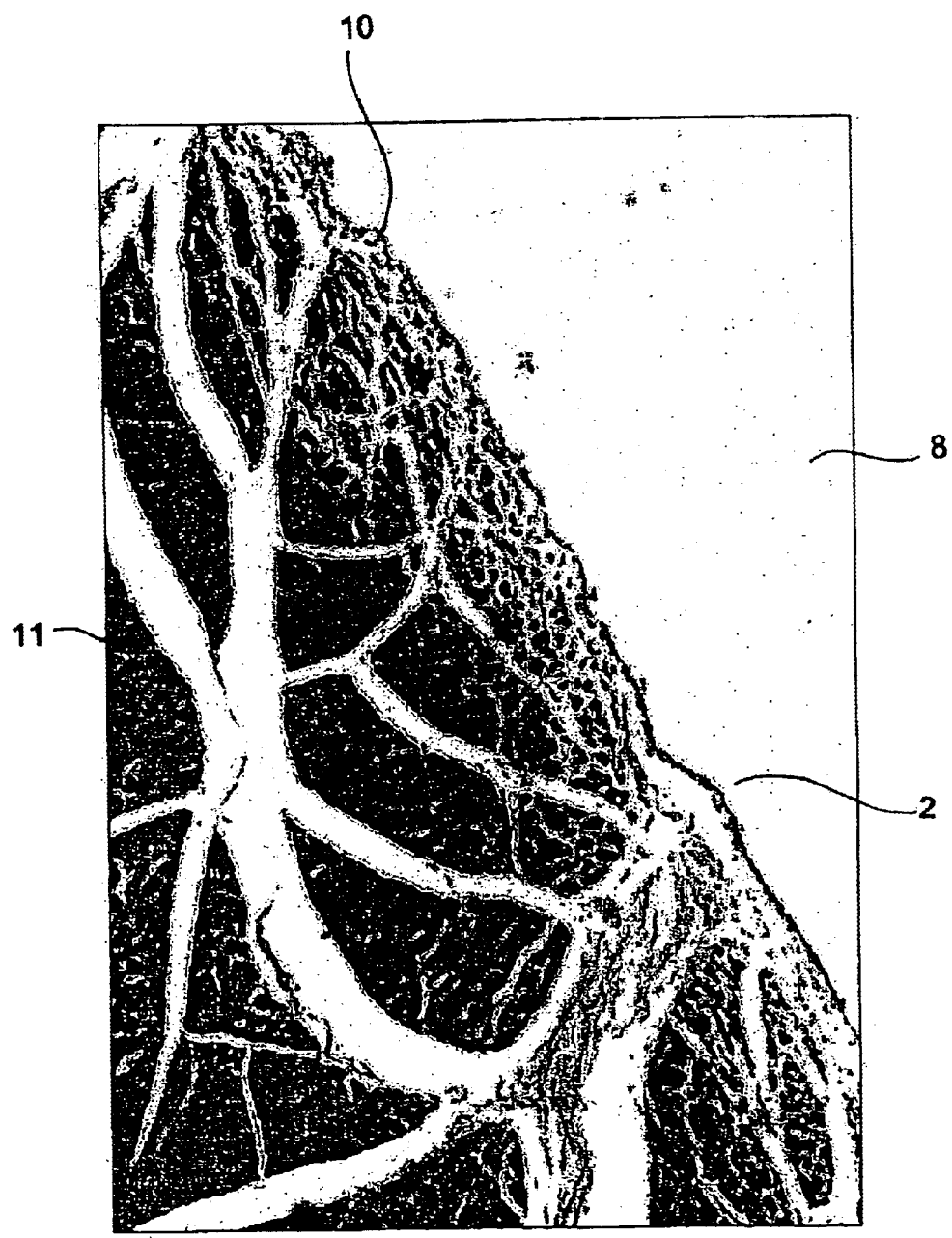
FIG. 7 is a microscopic photograph exhibiting another embodiment of an example of the present invention.
Figure 8:
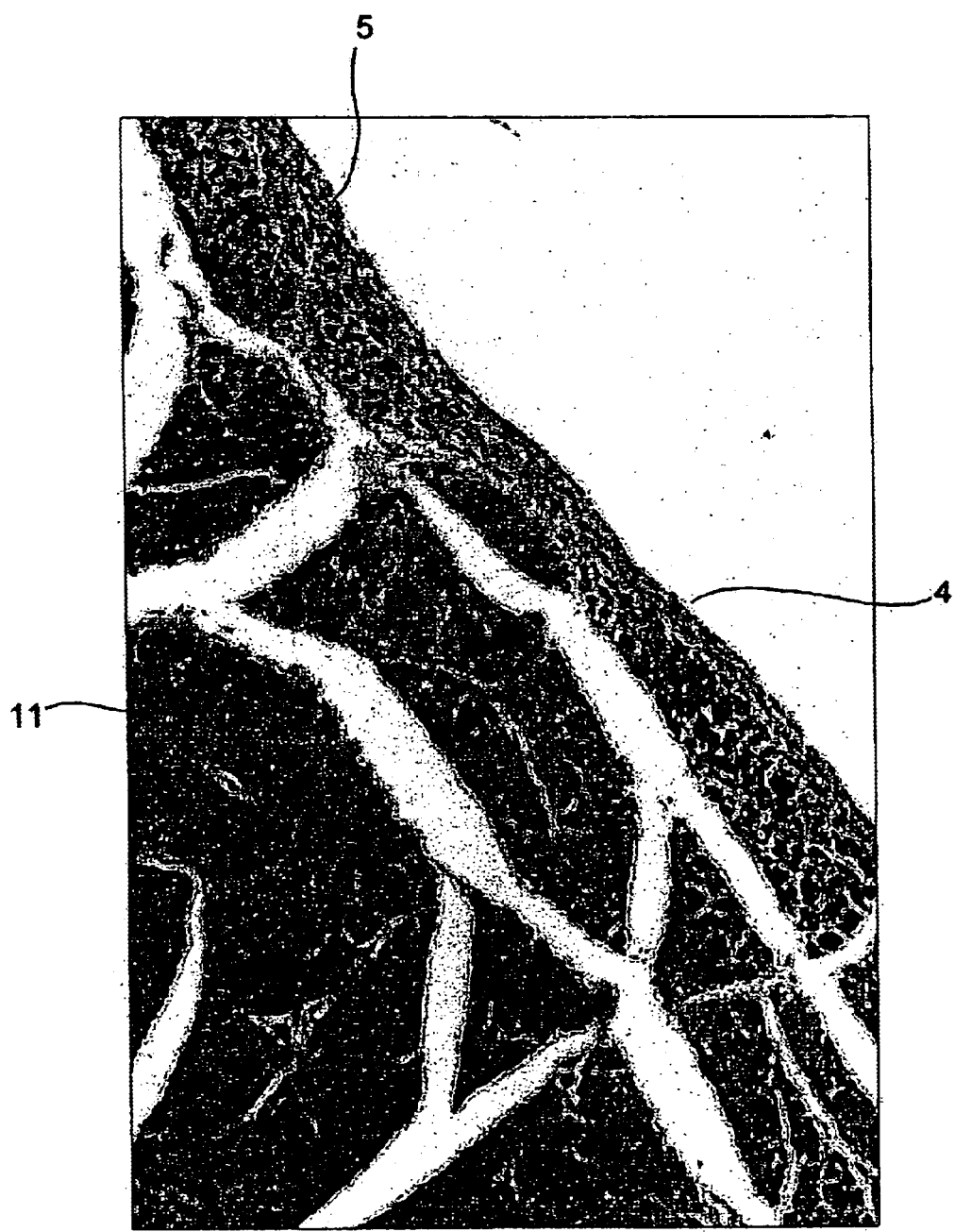
FIG. 8 is a microscopic photograph exhibiting another embodiment of an example of the present invention.

FIGS. 7 and 8 are photographs magnified 400 times which exhibits the reaction of living tissues when a barium titanate ceramic 8 treated by polarization is placed inside a living organ (liver of an adult beagle) for 7 days. In FIG. 7, formation of productive cells 10 is found at the N-surface 2. In FIG. 8, formation of cells similar to connecting tissues is found at the P-surface. 11 shows the liver tissue.

Figure 9:
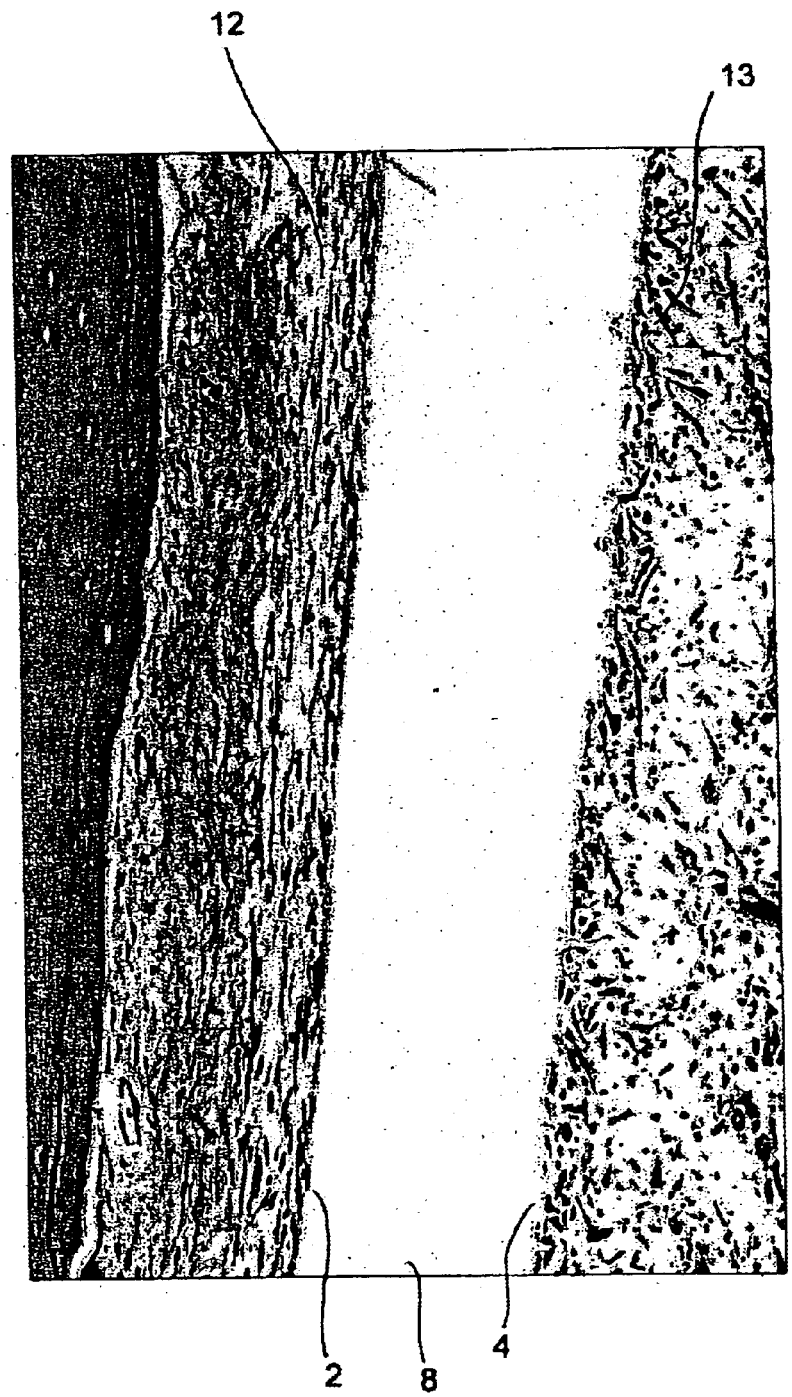
FIG. 9 is a microscopic photograph exhibiting another embodiment of an example of the present invention.

FIG. 9 is a photograph magnified 200 times which exhibits the reaction of living tissues when barium titanate ceramic treated by polarization 8 is placed inside a living organ (muscle of an adult beagle) for 7 days. At the N-surface 2, cells arranged in order 12 are formed. In contrast, cells arranged in disorder 13 are found at the P-surface.

Figure 10:
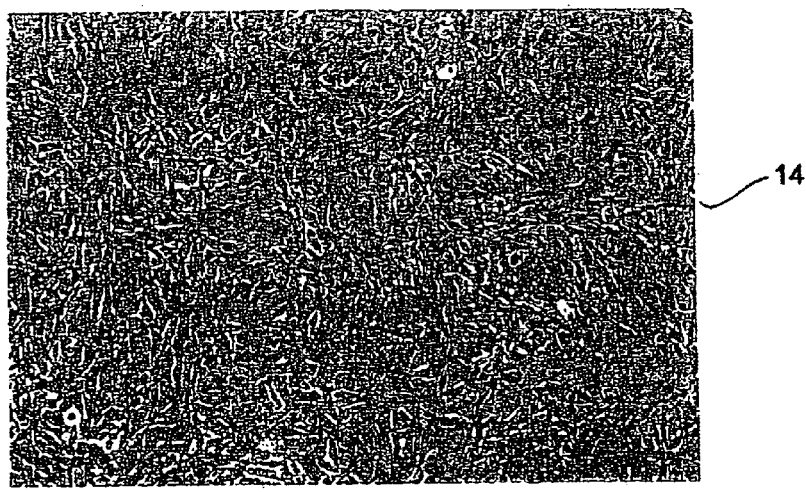
FIG. 10 is a microscopic photograph exhibiting an embodiment of another example of the present invention.
Figure 10:
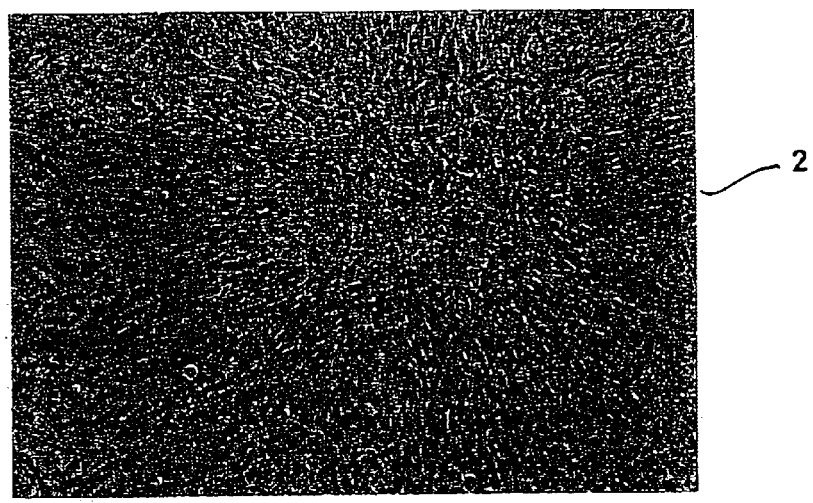
Figure 10:
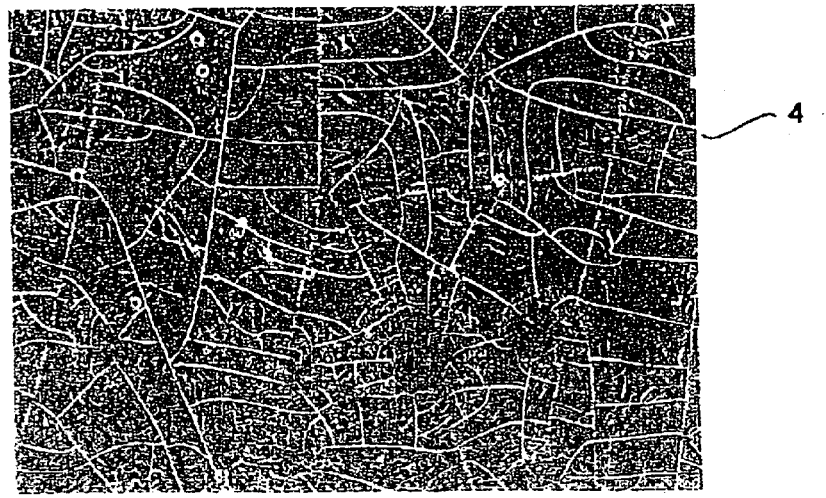

FIG. 10 shows phase-contrast microscopic photographs exhibiting behaviors of osteoblasts cultured for 73 hours in a glass cell culture dish coated with a hydroxyappatite ceramic which was not treated by polarization (the top photograph) and with a hydroxyappatite ceramic which was treated by polarization (the middle and bottom photographs). The coating was made in accordance with the sputtering method. In the top photograph exhibiting the cell culture dish which was not treated by polarization, the O-surface 14 is rough. In contrast, in the middle photograph exhibiting the cell culture dish which was treated by polarization, densely grown osteoblasts are found at the N-surface 2. At the P-surface 4 in the bottom photograph, the surface has cracks and almost no growth of osteoblasts can be found.

Figure 11:
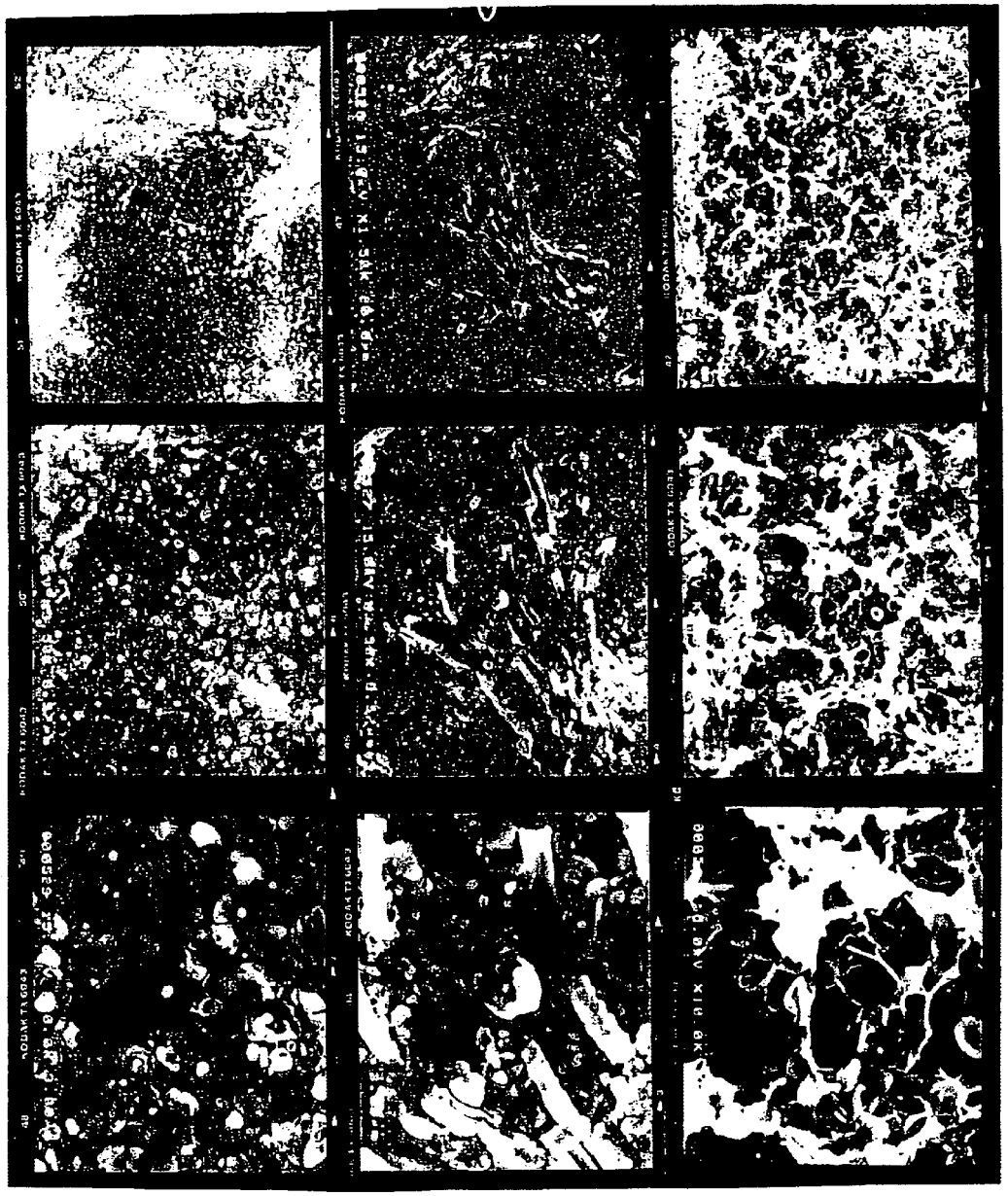
FIG. 11 is a microscopic photograph exhibiting another embodiment of another example of the present invention.

FIG. 11 shows photographs exhibiting the conditions of the surfaces of a strontium hydroxide appatite ceramic treated by polarization after being soaked into blood serum for 5 days. The photographs at the top row, the middle row and the bottom row exhibit the O-surface, the P-surface and the N-surface, respectively. The photographs at the left column, the middle column and the right column exhibit photographs magnified 100 times, 200 times and 400 times, respectively. At the O-surfaces 14 shown at the top row which were not polarized, osteocytes and proteins are adsorbed in disorder. Proteins are adsorbed at the P-surfaces 4 shown at the middle row and osteocytes are adsorbed at the N-surfaces 2 shown at the bottom row. This result shows that, when an implant material is coated with a layer of a ceramic treated by polarization which has suitable adsorption properties, drugs, nutrients and proteins are selectively adsorbed by utilizing the difference in the adsorption properties among the O-surface the P-surface and N-surface of the ceramic which are formed by treating the ceramic by polarization.

Figure 12:
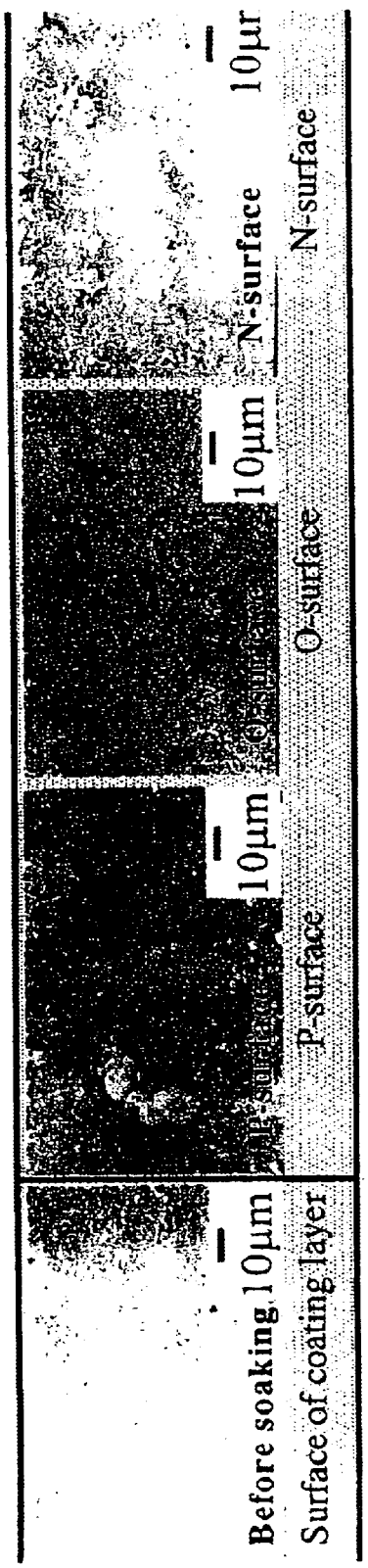
FIG. 12 is a microscopic photograph exhibiting an embodiment of another example of the present invention.

FIG. 12 shows photographs exhibiting the conditions of the surfaces of a hydroxyappatite ceramic coating film formed on a titanium substrate in accordance with the sputtering method. The left end photograph exhibits the conditions before being soaked into a simulated body fluid. The photographs at the middle left, the middle right and the right end exhibit the conditions of the P-surface, the O-surface and the N-surface, respectively, after being soaked into a simulated body fluid for 1 day. At the P-surface, proteins and scattered portions like osteoblasts are found. At the N-surface, numerous tissues like osteoblasts are found and various tissues are found in disorder.

In the sputtering method, gas molecules are positively ionized by a high voltage in a vacuum, accelerated to a high speed and clashed against a cathode (a target) such as powder and ceramics of hydroxyappatite and calcium phosphate. Particles discharged from the target coat a substrate such as a titanium substrate disposed at a position faced to the target.

Figure 13:
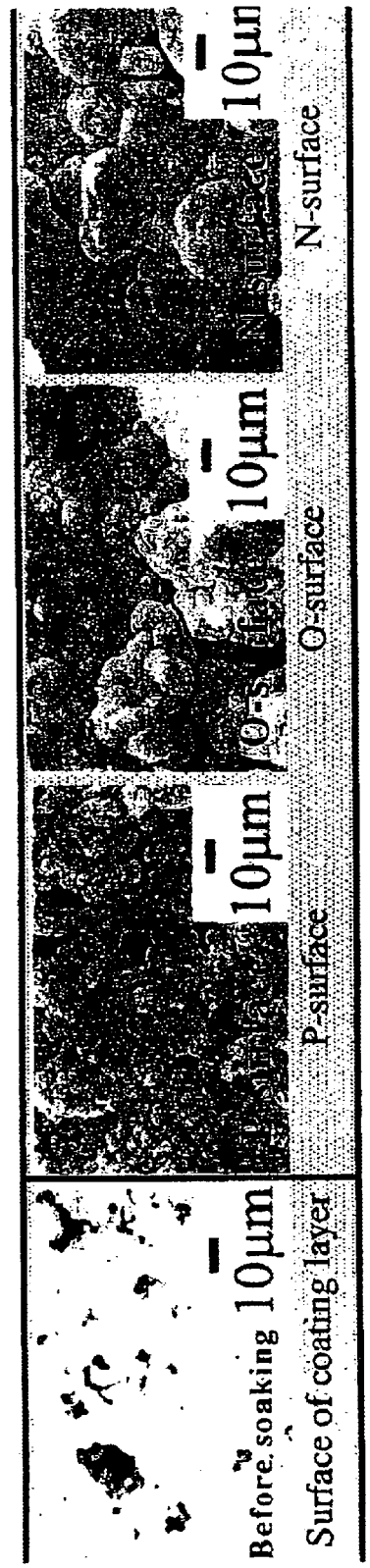
FIG. 13 is a microscopic photograph exhibiting another embodiment of another example of the present invention.

FIG. 13 shows photographs exhibiting the conditions of the surfaces of a hydroxyappatite ceramic coating films formed on a titanium substrate in accordance with the biomimetic method. The left end photograph exhibits the conditions before being soaked into a simulated body fluid. The photographs at the middle left, the middle right and the right end exhibit the conditions of the P-surface, the O-surface and the N-surface, respectively, after being soaked into a simulated body fluid for 1 day. At the P-surface, small portions like osteoblasts are found. At the N-surface, sufficiently grown up tissues like osteoblasts are found and tissues of intermediate sizes are found at the O-surface.

FIG. 14 shows photographs exhibiting the conditions of the surfaces of a hydroxyappatite ceramic coating films formed on a titanium substrate in accordance with the plasma spray method. The left end photograph exhibits the conditions before being soaked into a simulated body fluid. The photographs at the middle left, the middle right and the right end exhibit the conditions of the P-surface, the O-surface and the N-surface, respectively, after being soaked into a simulated body fluid for 1 day. At the P-surface and the O-surface, only small portions like cells are found. At the N-surface, sufficiently grown up tissues like osteoblasts are found.

In the plasma spray method, a ceramic in the condition of melting or close to melting is blown toward a substrate at a high speed to form a coating layer using an arc discharge as the means of melting and blowing. When a gas at a low temperature is introduced into the periphery of a plasma, the temperature of the central portion of the plasma jet reaches several ten thousands degrees centigrade. When powder of a hydroxyappatite having a particle diameter of several to several tens micrometers is introduced at a speed of several hundreds meters per second with a carrier gas, the object exposed to the stream is rapidly cooled at a rate of $10^4$ to $10^{6\circ}$ C./second and a film of a hydroxyappatite ceramic in the form of a lamella is formed at the substrate.

FIG. 15 shows photographs exhibiting the conditions of the surfaces of a needle-shaped hydroxyappatite ceramic coating film formed on a titanium substrate in accordance with the metal chelate dissociation method. The left end photograph exhibits the conditions before being soaked into a simulated body fluid. The photographs at the middle left, the middle right and the right end exhibit the conditions of the P-surface, the O-surface and the N-surface, respectively, after being soaked into a simulated body fluid for 2 days. At the P-surface and the O-surface, only small portions like cells which barely form needle shapes are found. At the N-surface, sufficiently grown up tissues like osteoblasts are found.

FIGS. 12 to 15 show the examples exhibiting that, when hydroxyappatite coating films are formed in accordance with various conventional coating methods showing affinity to biomaterials, the effect of the treatment by polarization can be obtained independently of the coating method adopted.

It has been confirmed by the present inventors that the effect of the treatment by polarization similar to that obtained by using barium titanate ceramics, strontium hydroxyappatite ceramics, hydroxyappatite ceramics containing calcium or strontium as solid solutions, lithium niobate ceramics, sodium niobate ceramics, potassium niobate ceramics, glasses and crystallized glasses which contain calcium phosphate, and various other materials including stabilized and partially stabilized zirconia ceramics, ion conductive alumina (so-called β-alumina) ceramics, and piezoelectric ceramics containing lead.

Figure 16:
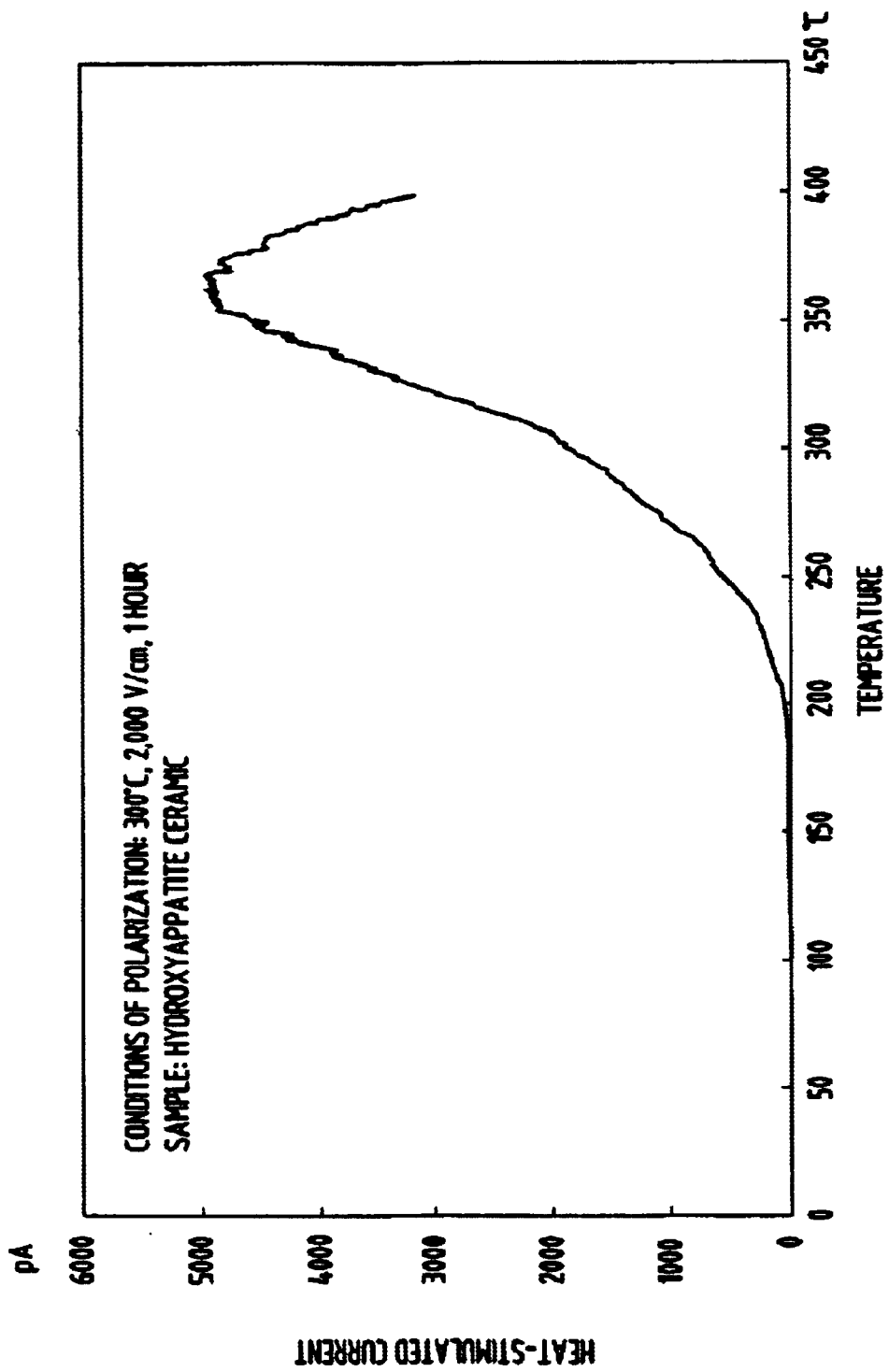
FIG. 16 is a diagram obtained by a measurement which exhibits the polarization energy in an example of the present invention.
Figure 17:
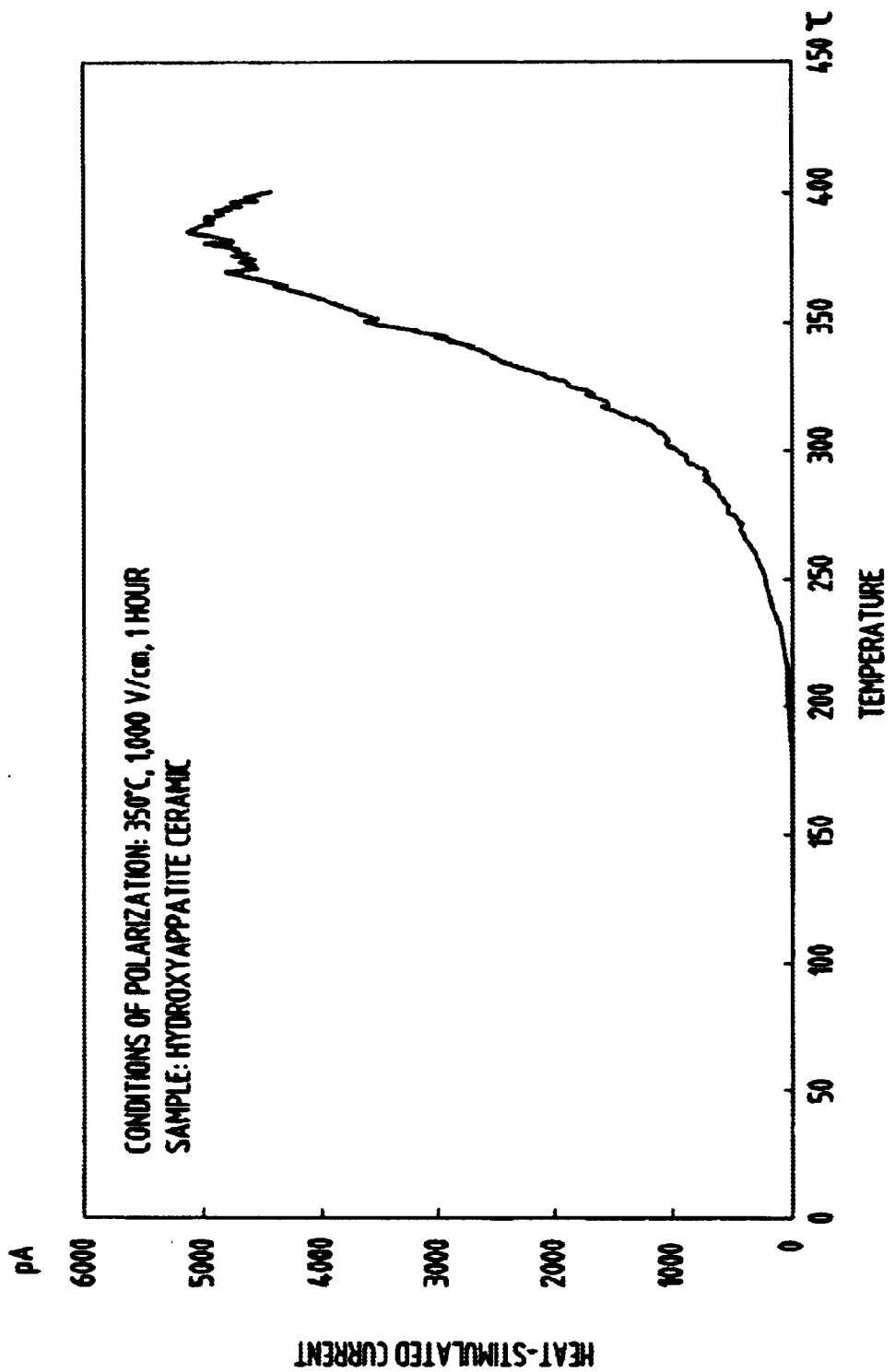
FIG. 17 is a diagram obtained by a measurement which exhibits the polarization energy in another example of the present invention.
Figure 18:
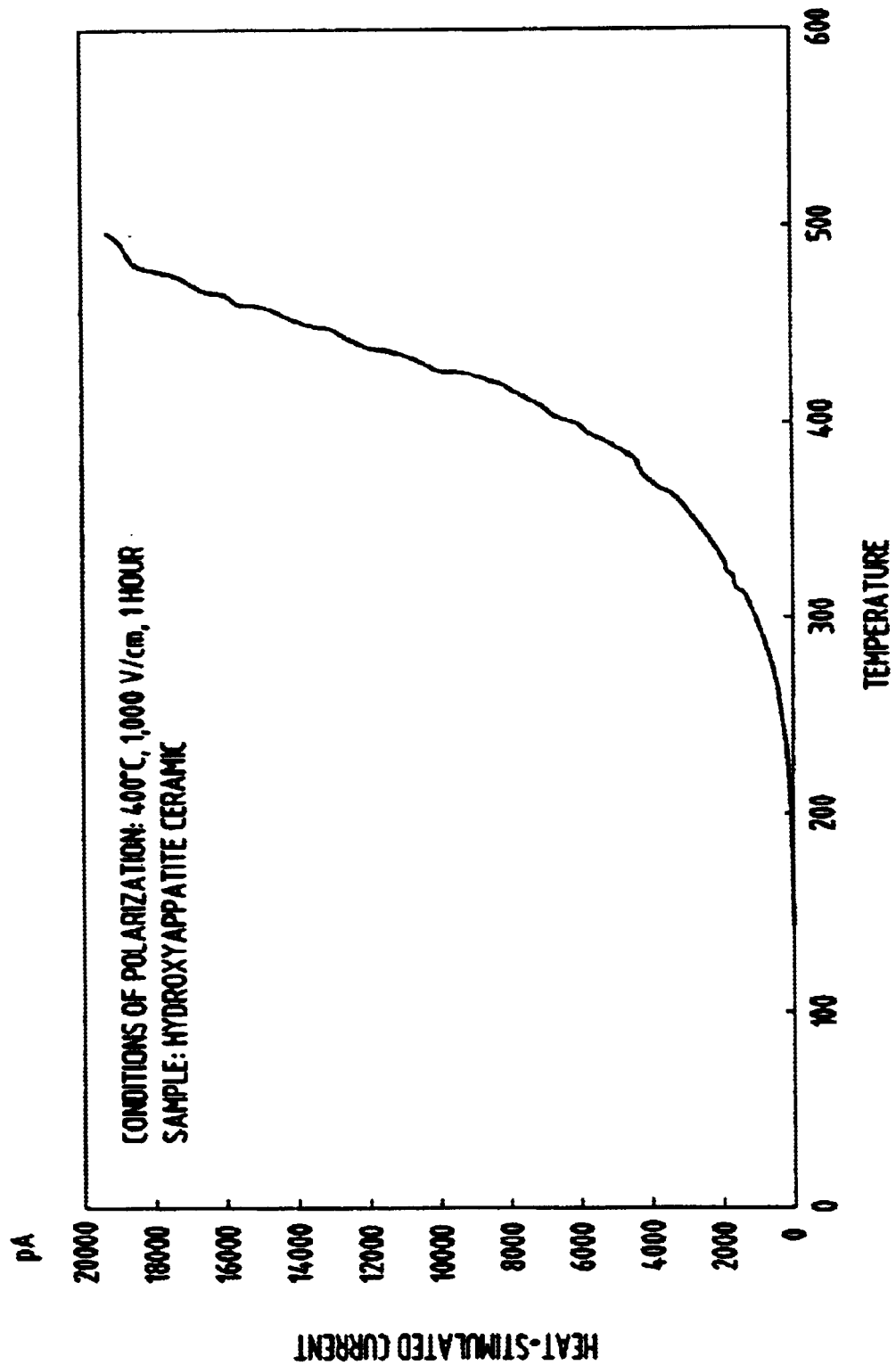
FIG. 18 is a diagram obtained by a measurement which exhibits the polarization energy in another example of the present invention.

FIGS. 16 to 18 are diagrams exhibiting the polarization energy stored in the hydroxyappatite ceramics treated by polarization. The energy (the polarization energy) stored by the polarization in the polarized ceramic is detected by measuring the heat-stimulated electric current which is generated by discharging the energy stored in the polarized ceramics by heating.

FIG. 16 shows a diagram exhibiting the polarization energy stored in a hydroxyappatite ceramic treated by polarization in the condition of 300° C., 2,000 V/cm and 1 hour in the atmosphere of steam. The peak value of the heat-stimulated electric current generated from the stored energy is about 5,000 pA (pico ampere).

FIG. 17 shows a diagram exhibiting the polarization energy stored in a hydroxyappatite ceramic treated by polarization in the condition of 350° C., 2,000 V/cm and 1 hour in the atmosphere of steam. The peak value of the heat-stimulated electric current generated from the stored energy is about 5,200 pA (pico ampere).

FIG. 18 shows a diagram exhibiting the polarization energy stored in a hydroxyappatite ceramic treated by polarization in the condition of 400° C., 2,000 V/cm and 1 hour in the atmosphere of steam. The peak value of the heat-stimulated electric current generated from the stored energy is greater than about 19,000 pA (pico ampere).

The optimum condition for the treatment by polarization is different depending on the type of the ceramic for the polarization and can be obtained in accordance with ordinary experimental methods. By comparing the diagram shown in FIG. 18 with the diagrams shown in FIGS. 16 and 17, the optimum condition for the treatment by polarization of the hydroxyappatite ceramic is obtained as: 400° C., 1,000 V/cm and 1 hour in the atmosphere of steam.

What is claimed is:

1. A method for controlling growth, inhibition of growth, activation or inactivation of a microorganism, comprising:

providing a ceramic having an N-surface and a P-surface that were formed by treating the ceramic by polarization; and adsorbing on at least one of the N-surface and P-surface a microorganism.

2. A method according to claim 1, wherein the ceramic is a material or a combination of materials selected from hydroxyappatite ceramics, barium titanate ceramics, strontium hydroxyappatite ceramics, hydroxyappatite ceramics containing calcium or strontium as solid solutions, lithium niobate ceramics, sodium niobate ceramics, potassium niobate ceramics, glasses and crystallized glasses which contain calcium phosphate, stabilized and partially stabilized zirconia ceramics, ion conductive alumina (so-called β-alumina) ceramics, and piezoelectric ceramics containing lead.

3. A method according to claim 1, wherein the ceramic is in the form of a powder, fiber, bulk or a coating film.

* * * * *